Figure 1:
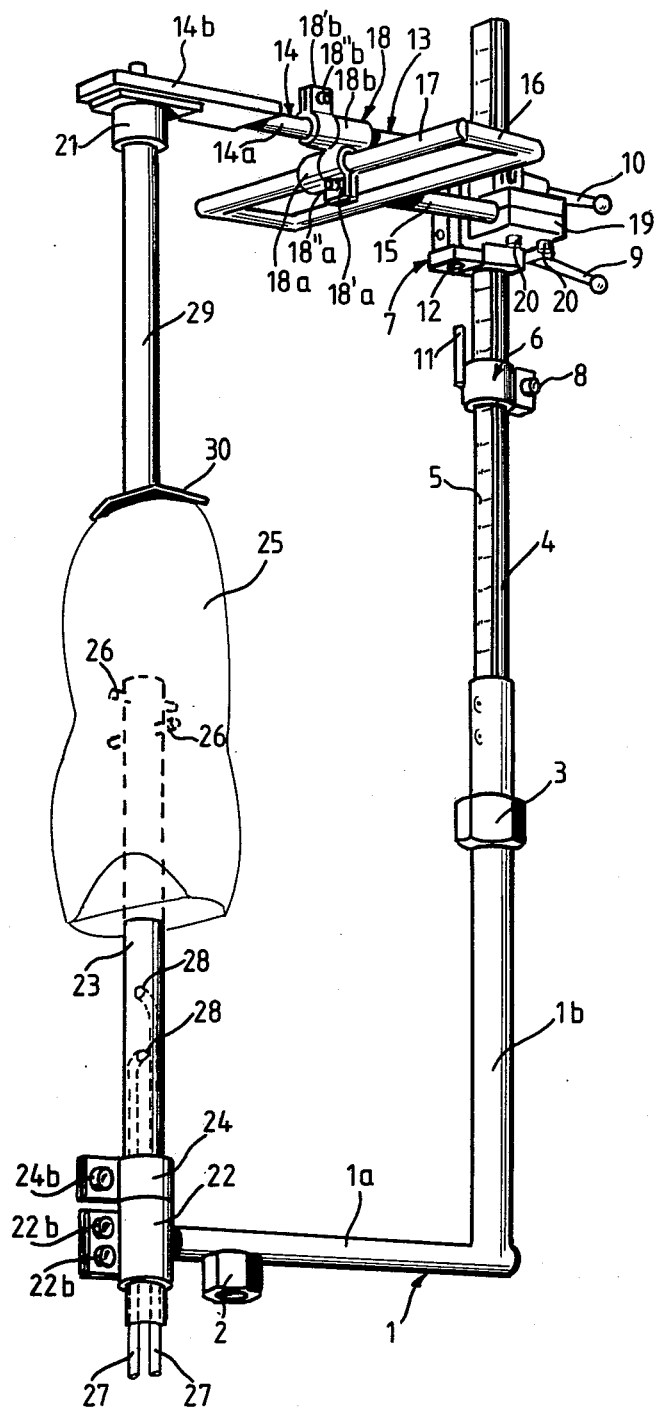

United States Patent [19]

Pettersson

[11] 4,314,398

[45] Feb. 9, 1982

[54] METHOD OF MAKING A LOWER LEG PROSTHESES

[75] Inventor: Torsten L. E. Pettersson, Upsala, Sweden

[73] Assignee: Een-Holmgren Ortopediska AB, Sweden

[21] Appl. No.: 61,037

[22] Filed: Jul. 26, 1979

[30] Foreign Application Priority Data

Jul. 27, 1978 [SE] Sweden .................. 7808174

[51] Int. Cl.³ .................. B23P 19/00; B23Q 3/00
[52] U.S. Cl. .................. 29/407; 3/17 R; 29/423; 29/428; 29/467
[58] Field of Search .................. 3/16, 17 R, 18, 19, 3/21; 29/407, 423, 428, 464, 467, 468; 264/40.1, 222, 223, 227

[56] References Cited

U.S. PATENT DOCUMENTS

| | | | |
|---|---|---|---|
| 1,907 | 3/1863 | Parmelee | 3/17 R |
| 37,637 | 2/1865 | Parmelee | 3/17 R |
| 1,907,511 | 5/1933 | Davies | 3/17 R |
| 2,594,751 | 4/1952 | Fahlstrom | 3/17 R |
| 3,377,416 | 4/1968 | Kandel | 3/19 X |
| 3,393,407 | 7/1968 | Kandel | 264/222 X |
| 3,422,462 | 1/1969 | Finnieston | 3/17 R |
| 4,128,903 | 12/1978 | Marsh et al. | 3/19 |

FOREIGN PATENT DOCUMENTS 2217261  3/1973  Fed. Rep. of Germany ............ 3/21

*Primary Examiner*—Ervin M. Combs
*Attorney, Agent, or Firm*—Bernard, Rothwell & Brown

[57] ABSTRACT

The invention relates to a method and a device for making lower leg prostheses, comprising a prosthesis sleeve, a prosthesis foot and a connecting member interconnecting said prosthesis sleeve and said prosthesis foot. In said method the desired position of said prosthesis foot in relation to said prosthesis sleeve is determined and a prosthesis sleeve is then formed on a prosthesis sleeve positive while simultaneously securing said connecting member to said prosthesis sleeve in the desired position.

A support device for use in said method comprises first fastening means for a support for said prosthesis sleeve positive and second fastening means for mounting adapter means for said prosthesis foot, said first and second fastening means being adjustable in relation to each other to permit reproducible setting of said fastening means corresponding to a desired positioning of said prosthesis foot to said prosthesis sleeve.

5 Claims, 2 Drawing Figures

METHOD OF MAKING A LOWER LEG PROSTHESES

The present invention relates to a new method of manufacturing lower leg prostheses, this method making it possible to obtain lighter prostheses than earlier while maintaining the strength and function thereof. The invention also relates to a device for use when practising the method.

Lower leg prostheses, i.e. prostheses which substitute leg parts lost below the knee joint, usually comprise a prosthesis sleeve or the like for the remaining leg stump below the knee. This sleeve is via a middle piece connected to a prosthesis foot. To allow the patient to walk as unimpededly as possible i.e. without subjecting e.g. the knee- and hip joints to additional strains, it is important to provide a correct adjustment of the prosthesis foot and the middle piece in relation to the prosthesis sleeve, said adjustment corresponding to that of the lost body part and taking into consideration such factors as if the patient is knock-kneed, bandy-legged, etc. This adjustment may be achieved by letting the patient test a prosthesis having an adjustment device placed between the prosthesis sleeve and the prosthesis foot. This device permits horizontal and vertical adjustment of the relation between the prosthesis sleeve and the prosthesis foot.

The adjustment device may form a permanent part of the prosthesis or alternatively be mounted thereto only temporarily. In the former case the adjustment device must be as light as possible in order to keep the weight of the prosthesis down, but this reduces the precision of the adjustment. Further, the adjustment may change during use due to the continuous load on the screw means or the like, by which the adjustment is controlled. Even if the weight of the adjustment device is reduced, the presence thereof still makes the prosthesis undesirably heavy, this being experienced as annoying by the patient. For these reasons it is generally preferred to proceed according to the second alternative, viz. to provisionally arrange said adjustment device—or testing instrument—in a temporarily assembled prosthesis, and to remove the device after adjustment of the foot part but before completion of the prosthesis.

In the latter case a lower leg prosthesis is usually manufactured according to this method by first making a plaster cast—a so-called plaster negative—of the leg stump, to which the prosthesis is to be attached. This cast is then used for making a so-called plaster positive, around which a prosthesis sleeve is cast using a suitable plastic material. A support for a testing instrument is provided in the lower part of the sleeve, and the testing instrument is attached to the support. The contemplated prosthesis foot is then via an adapter attached to one end of a tube piece, the other end being attached to the testing instrument. The prosthesis is then tried out by the patient, necessary adjustments of the testing instrument and of the length of said tube piece being made. A connecting member—the so-called ankle piece—is then inserted between the prosthesis sleeve and the foot part. In order to maintain the positioning of the prosthesis foot and the tube piece in relation to the prosthesis sleeve when removing the testing instrument, the prosthesis (with the prosthesis foot removed) is set up in an alignment jig, i.e. a device having horizontally displaceable fastening means for the mounting adapter of the prosthesis foot and for the prosthesis sleeve. The position of the fastening means is marked, the tube piece is disengaged from the foot adapter, and the fastening means are displaced horizontally on the jig. The testing instrument with the attached tube piece and the foot adapter are then removed. The testing instrument support in the lower part of the prosthesis sleeve is then sawn to form a flat surface for attachment of said ankle piece. The ankle piece, which is adapted to be attached to the prosthesis foot in the same way as the foot adapter, is fixed in corresponding fastening means on the jig and sawn to the proper length by a cut in the same plane as said first cut in the lower part of the prosthesis sleeve. The sectional surface of the ankle piece is then marked on the sectional surface of the prosthesis sleeve, and the two elements are glued together after having been dismounted from the jig. In this manner the positioning of the main axis of the connecting tube, established by means of the testing instrument, as well as the tried out tube length have been transferred to the new connecting member or ankle piece. Then the foot is mounted, and the prosthesis is given a natural shape. In order to reduce the weight of prosthesis is once again sawn apart at the previous glue joint and the ankle piece is hollowed out as much as is permitted by the strength requirements. The separated parts are glued together again, possibly after reinforcement of the joint by wedges or the like. For further reinforcement the whole prosthesis is finally coated with an armoured plastic layer and preferably also with a thin layer of plastic foam and natural-coloured calfskin.

As appears from the above, the conventional method of making lower leg prostheses is complex and time consuming, and it is also difficult to sufficiently reduce the weight of the prosthesis.

The present invention provides a new and simplified method and device for making lower leg prostheses of considerably reduced weight, while maintaining the precision and strength of the prior art prosthesis.

In the method according to the invention the position of the prosthesis foot in relation to the prosthesis sleeve is adjusted like in the prior art method. Then, however, at least part of said connecting member is directly cast or embedded in the prosthesis sleeve in the predetermined alignment in connection with the manufacture of said sleeve. The connecting member is preferably secured in the prothesis sleeve by vacuum casting. This makes it possible to use considerably lighter connecting members, such as tubes of light metal and the like, without for that reason reducing the strength properties. The manufacture of the prosthesis is also simplified, since several of the steps of the prior art method are eliminated, which inter alia means a substantial saving of time and labour.

The invention also provides an improved support device or jig for supporting and reproducibly locking the prosthesis parts in their predetermined mutual positions when making the lower leg prosthesis.

According to a first embodiment of the invention one proceeds in conventional manner, e.g. as described above, up to and including the adjustment test of the prosthesis by means of the testing instrument. The prosthesis is then placed in a device, which permits reproducible setting of the correct (i.e. tested out) mutual positions of prosthesis sleeve, the connecting tube and the foot adapter, after the prosthesis sleeve has been applied to the plaster positive in its original position. The prosthesis sleeve, the testing instrument and the connecting tube are removed, and a connecting member, of the proper length, e.g. a light metal tube, is attached to the foot adapter. A new prosthesis sleeve is then cast, the connecting tube being partly embedded and secured in the lower part of the prosthesis sleeve. The prosthesis can then be given the final shape, e.g. by means of plastic foam, and be completed in a manner known per se.

According to another embodiment of the invention the testing out of the prosthesis is made directly with the prosthesis negative, after the testing instrument, the connecting tube and the prosthesis foot have been applied. A positive is then formed from the negative, and the mutual positions of the prosthesis components obtained by the testing are reproducibly fixed in a suitable device as described above. The negative is removed, and the prosthesis sleeve with the attached connecting member is completed in accordance with the above described embodiment.

Figure 2:
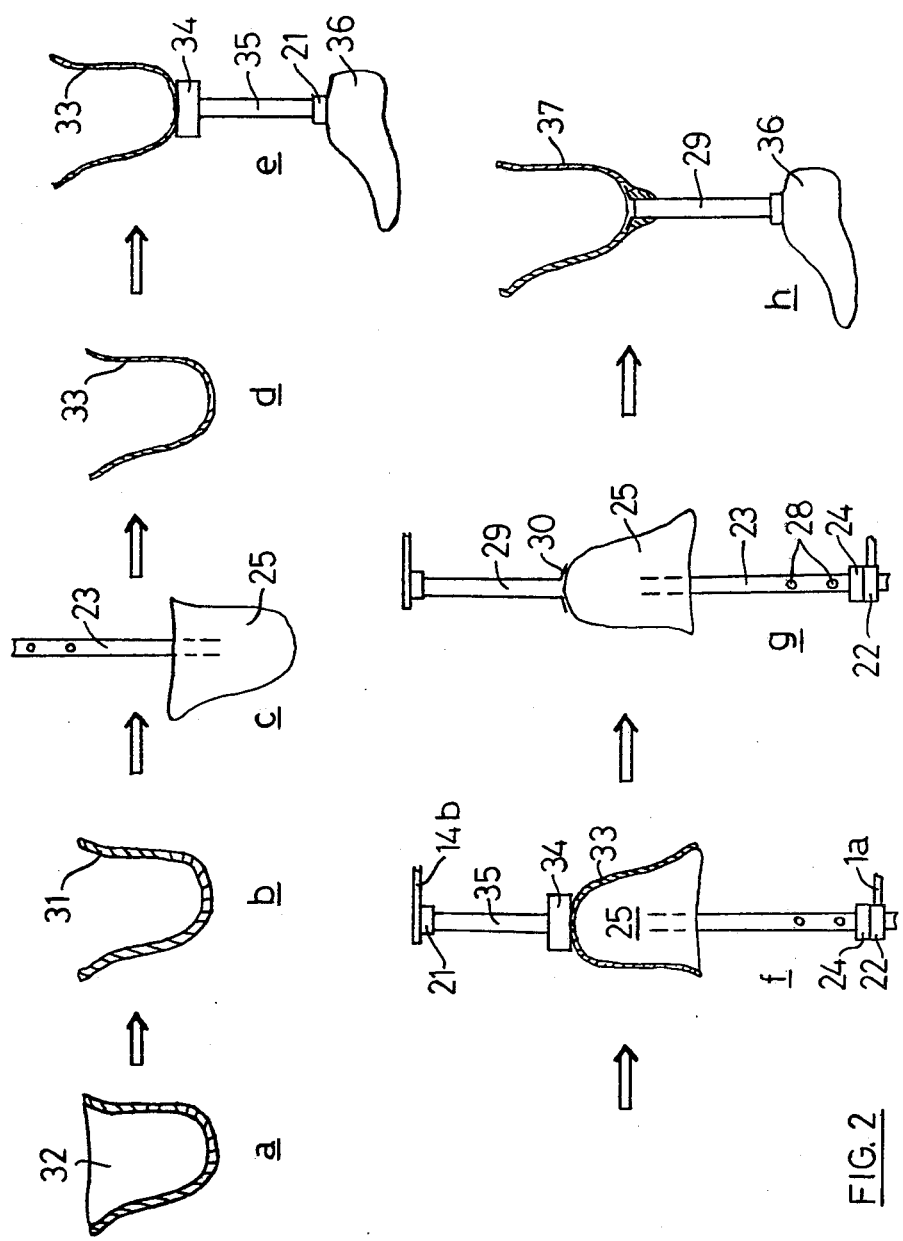

The invention will now be described in more detail with reference to the accompanying drawings in which FIG. 1 is a perspective view of one embodiment of a device for making lower leg prostheses in accordance with the invention, and FIG. 2 schematically illustrates the method according to the invention.

The device shown in FIG. 1 comprises an L-shaped support 1 having e.g. tubular support shanks 1a and 1b. The respective shanks 1a and 1b have attachment means 2 and 3 for fastening of the stand base 1 in a vise or the like. In the embodiment shown the attachment means 2 and 3 consist of hexagon rings welded on the shanks 1a and 1b respectively. A rod element 4 having a graded portion 5 extends from the shank 1b. The rod 4 carries lower and upper muff members 6 and 7 respectively, which can be displaced along the rod 4 and rotated around the same. The members 6 and 7 can be locked in arbitrary positions independently of each other by suitable lock means 8 in the lower muff member 6 and corresponding lock means 9 and 10 in the upper muff member 7. To this end the members 6 and 7 may, for example, be designed as so-called clamping sleeves, kept together by means of one or more adjustable boltings. Alternatively, they may consist of sleeves which can be locked against the support by set screws or the like. The bolts or screws may be provided with control levers such as the levers 9 and 10 of the upper muff member 7. The muff members 6 and 7 also have means for locking the two members against mutual rotation, for example male means 11 in the lower muff member 7 and corresponding female means 12 in the upper muff member 7. The upper muff member 7 further carries an adjustable holder 13 for a foot adapter holder 14. The holder 13 comprises a U-shaped bracket 16, which is secured to a shaft 15 carried by a clamping member 17 of the muff member 7. The bracket 16 carries a slide bar 17 for attachment means 18 for the foot adapter holder 14, said bar 17 being perpendicular to the shaft 15. The latter is movable in its longitudinal direction, essentially perpendicularly to the rod element 4, and it can be rotated about its longitudinal axis. The shaft 15 can be locked in desired positions by means of lock screws 20. The fastening means 18 comprise two muff members 18a and 18b arranged at right angles to each other and being ridigly secured to each other (or being integral with each other) at their central parts. The muff member 18a can be moved along and rotated about the slide bar 17, and it can be locked in arbitrary positions along said bar by means of a clamping portion 18′a and a lock screw 18″a. The foot adapter holder 14 comprises a shaft portion 14a and an end plate 14b provided with means for attachment of a foot adapter 21. The shaft 14a can be displaced and rotated in the muff member 18b, and it can be locked in arbitrary positions by means of a clamping portion 18′b with a lock screw 18″b.

It is not necessary to have the U-shaped bracket 16 of the holder 13 in the same plane as the shaft 15 (as shown), but the bracket 16 can e.g. be arranged at right angles to the shaft 15 ("vertically"). It is not either necessary to have the shaft 15 movable in the muff member 7, but it may be an integral part thereof.

The shank 1a is at its free end provided with means 22 for holding a support tube 23 essentially in parallel with the shank 1b and the rod element. The tube 23 can be displaced longitudinally and be turned about its longitudinal axis, and the holder 22 has means for locking the tube 23 in arbitrary positions. In the embodiment shown the holder 22 consists of a clamping sleeve with lock screws 22b. A muff member 24 can be moved along the tube 23, and be locked in arbitrary positions by means of a lock screw 24b. Male and female means (not shown) provided on the holder 22 and the member 24 respectively can lock said two parts against mutual rotation.

In FIG. 1 the tube 23 is shown as being partly embedded in a plaster positive 25 for a prosthesis sleeve and as being fixed in the holder 22. The embedded end portion of the tube 23 is provided with securing pins 26. Two smaller inner tubes 27 are arranged inside the tube 23, and they end in two openings 28, which are located above each other in the center portion of the tube 23. A foot adapter 21 for a prosthesis foot is fixed in the foot adapter holder 14. A connecting tube 29, intended to form a part of the completed prosthesis, is fixed in the adapter 21, e.g. by screwing or clamping. The opposite end of the connecting tube 29 is provided with a plate 30, which is slightly bent at two opposite ends and which for reasons explained below preferably is provided with slots or holes.

Since the support tube 23 may be subjected to rough treatment when making and finishing the plaster positive 25 (which may be detrimental to the fitting of the tube in the holder 22 and muff member 24), it may consist of two interconnected parts, viz. an upper part to be secured in the plaster positive 25 and a lower evacuation part to be used only when making the prosthesis. The upper part may, for example, have a smaller diameter than the lower part, so that it can be inserted into the latter and be fixed to the same with e.g. screws. The muff member 24 is in this case preferably a stationary part of the lower portion of the tube 23.

In the above described device particularly the adjustable holder 13 may be designed in many different ways, for example comprising two lockable ball joints for obtaining a corresponding adjustability.

The use of the above described device for making a lower leg prosthesis will be described below with reference to two examples of alternative embodiments of the method according to the invention illustrated in FIG. 2.

EXAMPLE 1

A plaster cast or negative 31 of the leg stump 32, to which the finished lower leg prosthesis is to be fixed, is made in conventional manner (FIG. 2a and b). A plaster positive 25 is then formed from said cast, while partly embedding the tube 23 in the plaster positive 25 as shown in FIG. 2c. The securing pins 26 (FIG. 1) serve to improve the joint between the tube 23 and the plaster positive 25. The tube 23 with the attached plaster positive 25 is inserted into the holder 22 and locked in the desired position by tightening of the lock screws 22b. When using a two part evacuation tube 23 the upper part is embedded in the plaster positive 25 and is fixed in the lower tube part 23 only when the plaster positive 25 is ready. A prosthesis sleeve, a so-called negative 33, is then formed from the plaster positive 25 by conventional vacuum casting techniques (FIG. 2d). If desired, an insert sleeve of e.g. a plastic foam material such as Campolit (Camp Scandinavia AB, Helsingborg, Sweden) can be applied on the plaster positive before forming the negative. In carrying out the vacuum casting a bag-like foil (closed at the top) is drawn over the plaster positive 25 and sealed against the tube 23 between the two evacuation openings 28. The thin foil is closely pressed against the positive 25 by connecting the upper opening 28 to a vacuum source. Suitable reinforcement layers such as Perlon (nylon 6) hoses, glass fiber webs or the like are applied on said foil. An outer foil is drawn over the reinforcement layers and is sealed against the tube 23 below the lower evacuation opening 28, a suitable curable, preferably liquid resin such as an epoxy resin being filled through the open upper end of the outer foil (the resin may be mixed with a suitable reinforcement replacing or complementing said separate reinforcement). The outer foil is then sealed and the lower opening 28 connected to vacuum, a desired resin layer being conveniently formed between the two foils. The resin layer is then allowed to solidify under vacuum, whereupon the completed prosthesis sleeve 33 is removed from the plastic positive 25. The removal may be facilitated by connecting the upper opening 28 to a pressure source. A conventional testing instrument 34 such as a Hosmer-instrument (A. J. Hosmer Corp., Campbell, Calif., USA) is then secured to the prosthesis sleeve 33. As is well known in the art such instruments permit adjustment in all directions (inclination, side or horizontal displacement, and rotation). The testing instrument may be secured directly to the prosthesis sleeve 33 by means of a mounting plate embedded therein, e.g. cast therein when making the prosthesis sleeve. Alternatively, the instrument 34 may be connected to the sleeve 33 via e.g. an intermediate layer of foam material formed on the sleeve 33. A connecting tube 35, which has a length adapted to the patient, is secured to the testing instrument 34, and a prosthesis foot 36 is secured to the tube 35 at the other end thereof by means of a foot adapter 21, thus completing a test prosthesis (FIG. 2e). This prosthesis is then tested by the patient by walking with it. In connection herewith the length of the connecting tube 35 is adjusted finally, and the testing instrument 34 is adjusted with regard to e.g. abduction, adduction and flexion. If necessary, the connecting tube 35 is displaced horizontally (or sidewards) in the instrument, and the foot rotation is adjusted. The foot 36 is then removed from the foot adapter 21, and the now tested out prosthesis is applied on the plaster positive 25 (if necessary after cleavage of the prosthesis sleeve) in the very position it had before it was removed from the same after the casting. This unit is then mounted in the support device 1, the support tube 23 being locked by the holder 22 and the positioning member 24 (FIG. 2f). The upper muff member 7 and the adjustable holder 13 are adjusted, so that the mounting plate 14b of the foot adapter holder 14 can be secured to the foot adapter 21. This adjustment is effected by disengaging the muff members 6, 7, 18a and 18b, placing the foot adapter holder portion 14b against the foot adapter 21 and adjusting the muff member 7 so that the foot adapter holder portion 14b is plane against the foot adapter 21. The muff member 7 is then locked in this position by the screws 9 and 10. The foot adapter 21 is secured to the foot adapter holder 14 by a center screw, and the screws 18"a, 18"b and 20 are tightened. The muff member 6 is then moved up against the muff member 7, so that the male means, or pin, 11 engages the corresponding female means, or hole, 21 in the muff member 7, the upper end of the muff member 6 contacting the lower end of the muff member 7. The muff member 6 is then locked in this position by tightening the lock screw 8. The parameters tested out for the test prosthesis have now been reproducibly fixed or set in the support device by the muff members 6 and 24. The foot adapter 21 is then released from the connecting tube of the test prosthesis. The muff member 7 is subsequently loosened from the rod element 4 by means of the control levers 9 and 10 and moved upwards to release the hole 12 from the pin 11. The foot adapter 21 leaves the end of the connecting tube 35 and is swung aside. The prosthesis sleeve 33 with the testing instrument 34 and the connecting tube 35 is then removed from the plaster positive 25, and a new connecting tube 29, e.g. of aluminium, provided with an end flange or plate 30, is fitted in between the foot adapter 21 and the plaster positive 25 (FIG. 1 and FIG. 2g). The connecting tube 29 is length adjusted to leave an interspace of a few millimeters between the plate 30 and the upper part of the plaster positive 25 when the muff member 7 (with the holder 13) is brought back to the set position, in which it rests against the muff member 6 with the male means 11 fitted into the female means 12. The muff 7 with the holder 13 are then once more brought aside or lifted off the rod element 4, and a cone-shaped inner foil, closed at the top, is drawn over the plaster positive 25 and sealed against the support tube 23 between the two evacuation openings 28 in the same way as described above in connection with FIG. 2d. Reinforcement such as a Perlon hose, glass fibre hose, glass fibre sheeting or the like is applied to said foil, and the connecting tube 29 is brought back to the set position by bringing the muff 7 into engagement with the muff 6. Additional reinforcement layers are applied over the plaster positive 25 and the adjacent part of the connecting tube 29. This reinforcement may, for example, consist of a Perlon hose, glass fibre hose, a glass fibre sheeting, strips of carbon fiber, or the like. Reinforcement strips are preferably drawn through the above mentioned slots in the plate 30. The foot adapter 21 is released from the connecting tube 29, and the muff member 7 (with the holder 13) is moved upwards and swung aside. A preferably cone-shaped outer foil is then drawn down over the connecting tube 29 and the plaster positive 25, which is sealed against the tube 23 below the lower one of the evacuation openings 28. The muff member 7 is then brought back to its set position, so that the connecting tube 29 is fitted into the foot adapter 21 and secured therein, the muff member 7 being locked against the rod element 4 by means of the locking bolts 9 and 10. A suitable curable resin such as an epoxy, polyester, or acrylic resin or the like is then applied between the outer and inner foils and is vacuum shaped by connecting the tubes 27 to a suitable vacuum source, as described above. In order to ensure that the resin also flows under the plate 30, the upper muff member 7 may at the beginning be kept somewhat above over the lower muff member 6 and then be brought to the above mentioned set position. When the resin has solidified, the connecting tube 29 is rigidly secured in the final prosthesis sleeve 37, and the positioning or alignment of the tube 29 and the foot adapter 21 is exactly the one tested out by means of the testing instrument 34. The foot adapter holder 14 is then released from the foot adapter 21, and the muff member 7 is loosened, lifted up and swung to the side. After removal from the plaster positive 25 and mounting the prosthesis foot 36 in the adapter 21 (FIG. 2h) it only remains to give the prosthesis the desired cosmetic or visual design in conventional manner, e.g. by applying a calf cone on the connecting tube 29 and by coating with e.g. leather or stocking.

In the above described embodiment it is obvious that also the support tube 23 may be released from the holder 22 after the positions of the connecting tube 29 and the foot adapter 21 have been determined and set. In the same way as for the muff members 6 and 7 also the adjustment of the tube 23 can be exactly reproduced by placing the muff member 24 against the holder 22, so that male means of the member 24 are fitted into female means of the holder 22 (or vice verse).

The above described procedure makes it possible to reduce the weight of the prosthesis by about 20–30% as compared to the prior art methods. Another advantage is that the final prosthesis sleeve can be made with the same thickness and stiffness as the corresponding sleeve in the test prosthesis. Furthermore, the method also eliminates certain steps, which are dangerous to the health, such as glueing and puttying, and it also is less time consuming than prior art methods giving a corresponding precision of the prosthesis.

Since the connecting tube 29 to a great extent determines the possible weight reduction of the prosthesis, the weight thereof may be reduced further by using modern construction materials with high strength and low weight, e.g. carbon fiber reinforced aluminium.

EXAMPLE 2

As in Example 1 a plaster negative is made from the leg stump, to which the prosthesis is to be attached (FIG. 2a and b). The test prosthesis (FIG. 2e) is then prepared directly, using the plaster negative 31 instead of the plastic negative or sleeve 33. In this case the test instrument 34 is preferably attached to the plaster negative via a suitable attachment plate being secured to the negative 31 by plastering or the like. The test prosthesis is tried out by the patient, and the necessary adjustments of the testing instrument is performed as in Example 1. A plaster positive 25 having a support tube 23 embedded therein is made in analogy with Example 1 (FIG. 2c). The plaster positive 25 with the attached test prosthesis (except the foot 36) is then used for setting the tested positions in analogy with Example 1 (FIG. 2f). The final prosthesis is then made as in Example 1 (FIGS. 2g and h).

It should be obvious to a person skilled in the art that this embodiment has several advantages. For example, the manufacturing time is considerably reduced, e.g. making it possible to have the prosthesis tested out by the patient on the same day as the plaster negative 31 is made.

The method and the device according to the invention are, of course, not restricted to the embodiments set forth or specifically described hereinbefore, but many variations and modifications are possible within the scope of the general inventive idea. For example, the invention can also be used for connecting members having a permanent adjustment device, the support device according to the invention making it possible to readily give the connecting member a very good initial positioning. The connecting member may also be secured to an already available prosthesis sleeve. Likewise the connecting member may consist of two (or possibly more) parts, in which case it only is necessary to secure one end part to the sleeve. This part may form merely an attachment means for the rest of the connecting member. Of course, the connecting member may have any other suitable shape than the above described tubular shape. Further, those parts of the support device which are adjustable by translation and/or rotation may be provided with suitable means permitting reading and reproduction of the set positions for each such part. This may be achieved by conventional length and angle graduation, but also electronically in a manner known per se. Provided that the plaster positive is preserved, a new prosthesis identical with the previous one may then be made without any preceding testing.

What I claim is:

1. A method of making a lower leg prosthesis, comprising a prosthesis socket, a prosthesis foot and a connecting member interconnecting said prosthesis socket and said prosthesis foot, said method comprising the steps of:
    (a) forming a temporary prosthesis socket having an inner shape substantially corresponding to the remaining lower leg stump of the amputee to which the prosthesis is to be attached,
    (b) forming a test prosthesis by fixing an adjustable position testing device to said temporary socket and connecting said testing device to said prosthesis foot through a temporary connecting member,
    (c) testing said test prosthesis on the patient and adjusting said testing device so as to obtain a proper individually adjusted alignment of said temporary socket in relation to said prothesis foot,
    (d) providing a prosthesis socket positive in the temporary socket of said test prosthesis and reproducibly fixing the assembly comprised of the socket positive, the temporary socket, the testing device and at least the temporary connnecting member in a support device,
    (e) removing the test prosthesis parts from said support device,
    (f) placing said connecting member adjacent said socket positive in the support device in the aligned relative position reproducibly set in the support device in step (d), and
    (g) forming said prosthesis socket on said socket positive while simultaneously securing said connecting member to the prosthesis socket in said aligned relationship thereby obtaining an individually aligned lower leg prosthesis.

2. A method according to claim 1, wherein said temporary prosthesis socket is a socket formed on said prosthesis socket positive.

3. A method according to claim 1, wherein said temporary prosthesis socket is formed directly on said remaining leg stump of the amputee, and wherein in step (d) said prosthesis socket positive is formed in the temporary socket.

4. A method according to claim 1, wherein said prosthesis foot is connected to said temporary connecting member and connecting member, through mounting adapter means, and wherein the prosthesis foot is removed from said mounting adapter means before the test prosthesis of step (b) is fixed in the support device in step (d).

5. A method according to claim 1, wherein the making of said sockets comprises vacuum casting of a curable resin.

* * * * *